US012797194B2

(12) United States Patent
Wang

(10) Patent No.: US 12,797,194 B2
(45) Date of Patent: Nov. 17, 2026

(54) TISSUE CLOSURE DEVICE

(71) Applicant: SHENZHEN LIFEVALVE MEDICAL SCIENTIFIC CO., LTD., Shenzhen (CN)

(72) Inventor: Gang Wang, Shenzhen (CN)

(73) Assignee: SHENZHEN LIFEVALVE MEDICAL SCIENTIFIC CO., LTD., Shenzhen (CN)

( * ) Notice: Subject to any disclaimer, the term of this patent is extended or adjusted under 35 U.S.C. 154(b) by 753 days.

(21) Appl. No.: 18/250,167

(22) PCT Filed: Sep. 8, 2021

(86) PCT No.: PCT/CN2021/117216
§ 371 (c)(1),
(2) Date: Apr. 21, 2023

(87) PCT Pub. No.: WO2022/095586
PCT Pub. Date: May 12, 2022

(65) Prior Publication Data

US 2023/0397990 A1 Dec. 14, 2023

(30) Foreign Application Priority Data

Nov. 3, 2020 (CN) ......................... 202011209042.8
Nov. 3, 2020 (CN) ......................... 202011212602.5

(51) Int. Cl.
*A61B 17/122* (2006.01)
*A61B 17/128* (2006.01)
(Continued)

(52) U.S. Cl.
CPC ............ *A61F 2/246* (2013.01); *A61B 17/122* (2013.01); *A61B 17/1285* (2013.01); *A61B 2017/00584* (2013.01); *A61F 2/2466* (2013.01)

(58) Field of Classification Search
CPC .... A61F 2/246; A61F 2/2466; A61B 17/1285; A61B 17/122; A61B 17/0057;
(Continued)

(56) References Cited

U.S. PATENT DOCUMENTS 7,635,329 B2 * 12/2009 Goldfarb ................ A61B 17/29 600/37
7,811,296 B2 * 10/2010 Goldfarb ................ A61F 2/246 606/151
(Continued)

FOREIGN PATENT DOCUMENTS

CN 109717987 A 5/2019
CN 109953779 A 7/2019
(Continued)

OTHER PUBLICATIONS

International Search Report issued on Dec. 14, 2021, in corresponding to International Patent Application No. PCT/CN2021/117216, 7 pages.

(Continued)

*Primary Examiner* — Andrew Restaino
*Assistant Examiner* — Mitchell Brian Hoag
(74) *Attorney, Agent, or Firm* — Maier & Maier, PLLC

(57) ABSTRACT

A tissue closure device includes first and second clamping parts configured to clamp tissue. The first clamping parts include a first clamping arm and a supporting arm rotatably connected to the first clamping arm, and the supporting arm includes a curved section and a straight section. One end of the curved section is fixedly connected to the straight section, and the other end is rotatably connected to the first clamping arm. Alternatively, an end of the curved section is fixedly connected to the straight section, and an end of the straight section away from the curved section is rotatably connected to the first clamping arm. The first clamping arm
(Continued)

and the supporting arm are movable between open and closed positions, and when the first clamping arm and the supporting arm are in the closed position, the first clamping arm and the second clamping part are close to each other.

10 Claims, 11 Drawing Sheets

(51) Int. Cl.
*A61F 2/24* (2006.01)
*A61B 17/00* (2006.01)

(58) Field of Classification Search
CPC ................................ A61B 2017/00584; A61B 2017/00588–00632; A61B 2017/00637; A61B 2017/00646; A61B 2017/00654; A61B 2017/00659; A61B 2017/00575; A61B 2017/00884
See application file for complete search history.

(56) References Cited

U.S. PATENT DOCUMENTS

| | | | | |
|---|---|---|---|---|
| 8,052,592 | B2 * | 11/2011 | Goldfarb | A61F 2/246 600/37 |
| 8,303,608 | B2 * | 11/2012 | Goldfarb | A61B 17/1285 606/151 |
| 8,945,177 | B2 * | 2/2015 | Dell | A61B 17/08 606/151 |
| 9,011,468 | B2 * | 4/2015 | Ketai | A61B 17/08 606/198 |
| 10,105,222 | B1 * | 10/2018 | Metchik | A61F 2/246 |
| 10,245,144 | B1 * | 4/2019 | Metchik | A61B 17/122 |
| 11,185,413 | B2 * | 11/2021 | Basude | A61F 2/2463 |
| 12,653,672 | B2 * | 6/2026 | Hamill | A61B 17/0401 |
| 2004/0049207 | A1 * | 3/2004 | Goldfarb | A61F 2/2463 606/139 |
| 2011/0066180 | A1 * | 3/2011 | Zeng | A61B 17/0057 606/213 |
| 2015/0148896 | A1 * | 5/2015 | Karapetian | A61F 2/246 623/2.11 |
| 2018/0161159 | A1 | 6/2018 | Lee et al. | |
| 2019/0069991 | A1 * | 3/2019 | Metchik | A61F 2/246 |
| 2019/0105046 | A1 | 4/2019 | Jagelski et al. | |
| 2019/0209293 | A1 * | 7/2019 | Metchik | A61F 2/246 |
| 2019/0261997 | A1 * | 8/2019 | Goldfarb | A61M 25/0138 |
| 2021/0361416 | A1 * | 11/2021 | Stearns | A61F 2/2466 |
| 2022/0133327 | A1 * | 5/2022 | Zhang | A61B 17/122 606/142 |
| 2022/0296248 | A1 * | 9/2022 | Abunassar | A61B 17/1285 |

FOREIGN PATENT DOCUMENTS

| | | | |
|---|---|---|---|
| CN | 111200995 | A | 5/2020 |
| CN | 111449805 | A | 7/2020 |
| CN | 111772875 | A | 10/2020 |
| CN | 213722143 | U | 7/2021 |
| CN | 113331996 | A | 9/2021 |
| WO | 2020167677 | A1 | 8/2020 |

OTHER PUBLICATIONS

Office Action issued on Jun. 28, 2024, in corresponding Chinese Application No. 202011209042.8, 8 pages.
Partial Supplementary European Search Report issued on Sep. 3, 2024, in corresponding European Application No. 21888285.0, 12 pages.
Office Action issued on Aug. 31, 2023, in corresponding Chinese Application No. 2021109571018, 12 pages, partial English translation attached.

* cited by examiner

TISSUE CLOSURE DEVICE

TECHNICAL FIELD

The embodiments relate to the field of interventional medical devices and to a tissue closure device.

BACKGROUND

This section merely provides background information which is not necessarily prior art.

Mitral valve diseases are commonly seen among the elderly, including mitral regurgitation and mitral stenosis which are usually seen, and of which the mitral regurgitation is mostly common. According to statistics, the incidence of mitral regurgitation reaches up to 10% among people over 75 years old. Mild mitral regurgitation generally has no effect on normal life, while moderate or severe mitral regurgitation requires intervention. Thoracotomy is a traditional surgical treatment which, with the support of extracorporeal circulation machine, opens the heart to repair or replace the valve. However, the high-risk patients cannot tolerate it. The interventional therapy which arose in recent years has brought hope to high-risk patients with mitral regurgitation. The interventional therapy generally transports a device through a catheter to the site of lesion to repair or replace the valve. At present, most of transcatheter mitral valve replacement products are in clinical research stage, while several transcatheter mitral valve repair products have been marketed.

The principle of existing transcatheter mitral valve repair products is to clamp the anterior and posterior leaflets of the mitral valve using a clamping device so as to reduce the valve opening area and achieve the purpose of treating regurgitation. Among the existing products, there are some clamping devices with a mechanical lock, which need to open the lock in the interventional operation to perform the clamping operation, resulting in a complicated operation. Further, since the clamping stress is uncontrollable due to the mechanical lock, the devices may cause great damage to valve leaflets. In order to avoid this problem, some products adopt elastic clamping method to clamp the valve leaflets between the elastic clamping arm and the flexible spacer so as to soften the clamping stress on valve leaflets and reduce valve leaflet damages. However, when the elastic clamping arm is used, it is necessary to spread the clamping arm using some mechanism before the valve leaflets are captured. A large force may be required in the opening process of spreading the clamping arm by a supporting arm, which may increase the surgical risk.

SUMMARY

Based on the foregoing, there is a need to provide a tissue closure device that is easy to open.

A tissue closure device includes first clamping parts and second clamping parts configured to clamp tissue. Each of the first clamping parts includes a first clamping arm and a supporting arm rotatably connected to the first clamping arm, and the supporting arm includes a curved section and a straight section. One end of the curved section is fixedly connected to the straight section, and the other end is rotatably connected to the first clamping arm. Alternatively, an end of the curved section is fixedly connected to the straight section, and an end of the straight section away from the curved section is rotatably connected to the first clamping arm. The first clamping arm and the supporting arm are movable between an open position and a closed position, and when the first clamping arm and the supporting arm are in the closed position, the first clamping arm and the second clamping part are close to each other.

In one embodiment, the curved section is curved in the closed position, and the degree of curvature of the curved section increases as the first clamping arm and the supporting arm move from the closed position to the open position.

In one embodiment, an arc length of the curved section is ⅕ to ⅓ of a length of the straight section.

In one embodiment, the curved section has an angle between 10 and 45 degrees.

In one embodiment, the tissue closure device further includes a first fixing base and a second fixing base, where an end of the first clamping arm away from the supporting arm is fixedly connected to the first fixing base, and an end of the supporting arm away from the first clamping arm is rotatably connected to the second fixing base.

In one embodiment, the supporting arm includes a supporting body and a connecting portion connected to the supporting body, where an end of the connecting portion away from the supporting body is connected to the first clamping arm, and an end of the supporting body away from the connecting portion is rotatably connected to the second fixing base.

In one embodiment, each of the second clamping parts includes a second clamping arm, where one end of the second clamping arm is fixedly connected to the second fixing base, and the other end is a free end. Alternatively, one end of the second clamping arm is connected to an end of the supporting arm away from the first clamping arm, and the other end is a free end.

In one embodiment, the tissue closure device further includes a spacer having one end fixedly connected to the second fixing base and the other end extending axially in a direction away from the second fixing base.

In one embodiment, the tissue closure device further includes a guide tube arranged in the spacer.

In one embodiment, each of the second clamping parts includes a second clamping arm having an anchor arranged thereon.

A tissue closure device includes first clamping parts and second clamping parts configured to clamp tissue. Each of the first clamping parts includes a first clamping arm including a connecting section and two supporting sections, where two ends of the connecting section are separately connected to the two supporting sections, and the end where the connecting section is located is a free end of the first clamping arm. Each of the supporting sections includes a curved segment and an extending segment. One end of the curved segment is connected to the extending segment, and the other end is connected to the connecting section. An end of the curved segment away from the extending segment is not in the same plane as the extending segment, so that the connecting section is away from the longitudinal central axis of the tissue closure device.

In one embodiment, the extending segment includes a curved rod and a straight rod connected to the curved rod, where an end of the curved rod away from the straight rod is connected to the curved segment.

In one embodiment, there are two first clamping parts and two second clamping parts, where a connection region of the curved rod with the curved segment of one first clamping arm abuts against a connection region of the curved rod with the curved segment of the other first clamping arm.

In one embodiment, each of the first clamping parts further includes a supporting arm having an end rotatably connected to the connecting section.

In one embodiment, the supporting arm includes a supporting body including a curved section and a straight section. One end of the curved section is fixedly connected to the straight section, and the other end is rotatably connected to the first clamping arm. Alternatively, an end of the curved section is fixedly connected to the straight section, and an end of the straight section away from the curved section is rotatably connected to the first clamping arm. The first clamping arm and the supporting arm are movable between an open position and a closed position, and when the first clamping arm and the supporting arm are in the closed position, the first clamping arm and the second clamping part are close to each other.

In one embodiment, the tissue closure device further includes a first fixing base and a second fixing base, where an end of the first clamping arm away from the supporting arm is fixedly connected to the first fixing base, and an end of the supporting arm away from the first clamping arm is rotatably connected to the second fixing base.

In one embodiment, the supporting arm further includes a connecting portion connected to the supporting body, where an end of the connecting portion away from the supporting body is connected to the first clamping arm, and an end of the supporting body away from the connecting portion is rotatably connected to the second fixing base.

In one embodiment, the curved rod has an angle between 5 and 15 degrees.

In one embodiment, the curved segment has an angle between 10 and 60 degrees.

In one embodiment, the tissue closure device further includes a spacer having one end fixedly connected to the second fixing base and the other end extending axially in a direction away from the second fixing base.

In one embodiment, the two first clamping parts are arranged around and outside the spacer and the two second clamping parts are arranged around and outside the spacer.

During implantation, the first clamping arms and the supporting arms change from a closed position to an open position. After capturing the tissue, the first clamping arms and the supporting arms change from the open position to the closed position such that the first clamping arms and the second clamping parts get close to each other so that the tissue is clamped between the first clamping arms and the second clamping parts. Since the supporting arms of the tissue closure device include curved sections and straight sections, the component forces applied by the supporting arms in the opening directions of the first clamping arms are increased during the opening process, so that the first clamping arms are opened more easily, thereby improving the safety of the manipulation system.

During implantation, the first clamping arms change from a closed position to an open position. After capturing the tissue, the first clamping arms change from the open position to the closed position such that the first clamping parts and the second clamping parts get close to each other so that the tissue is clamped between the first clamping parts and the second clamping parts. Since the ends of the curved segments of the first clamping arms away from the extending segments are not in the same planes as the extending segments, the connecting sections located at the free ends are away from the longitudinal central axis of the tissue closure device, so that the first clamping arms are opened more easily, allowing the first clamping arms to be opened by moving the connecting sections away from the longitudinal central axis with less force, thereby reducing the surgical risk.

DETAILED DESCRIPTION OF THE EMBODIMENTS

In order to make the above objects, features, and advantages clearer and understandable, the following embodiments are described in detail with reference to the accompanying drawings. In the following description, numerous details are set forth to provide a thorough understanding of the embodiments. While the embodiments may be embodied in many other forms other than those described herein, those skilled in the art may make similar modifications without departing from the spirit of the embodiments, and the embodiments are therefore not limited to the embodiments described below.

Unless defined otherwise, all technical and scientific terms used herein have the same meaning as commonly understood by one of ordinary skill in the art to which the embodiments belong. The terms are used herein in the description of the embodiments for the purpose of describing the embodiments only and are not intended as limiting.

Figure 1:
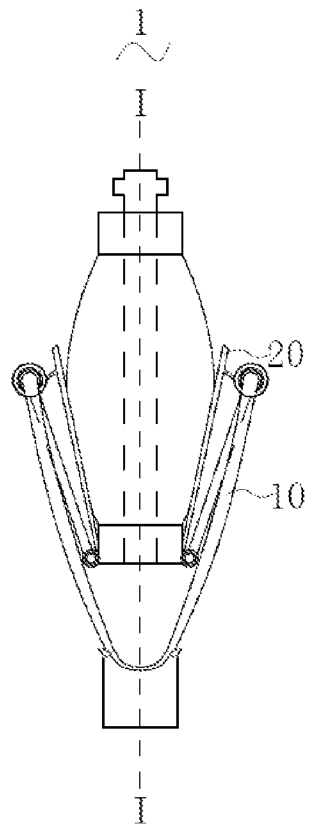
FIG. 1 is a structural diagram of a tissue closure device in a closed state according to an embodiment.

Referring to FIG. 1, a tissue closure system of an embodiment includes a tissue closure device 1 and a transporter. The tissue closure device 1 includes first clamping parts 10 and second clamping parts 20 configured to clamp tissue. The tissue is clamped between the first clamping parts 10 and the second clamping parts 20. The tissues include, but are not limited to, the leaflets of the mitral valve, the leaflets of the tricuspid valve, and the like.

There are at least two first clamping parts 10 and at least two second clamping parts 20, and the first clamping parts 10 and the second clamping parts 20 are equal in number. The tissue closure device 1 has a longitudinal central axis I-I, and two first clamping parts 10 are arranged symmetrically with the longitudinal central axis I-I as a symmetry axis and two second clamping parts 20 are arranged symmetrically with the longitudinal central axis I-I as a symmetry axis. It is understood that the first clamping parts 10 and the second clamping parts 20 are in one-to-one correspondence to clamp the tissue.

Figure 2:
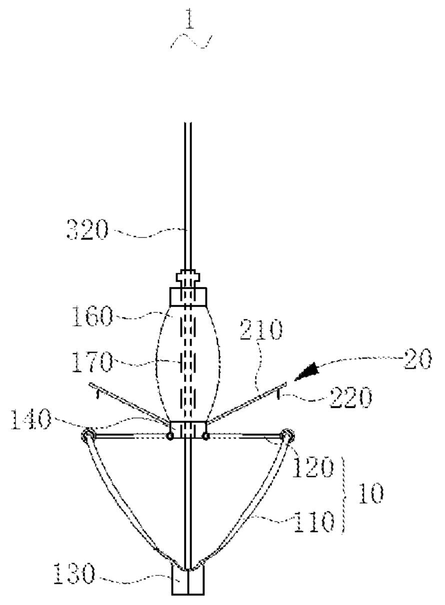
FIG. 2 is a structural diagram of a tissue closure device in an open state according to an embodiment.

Referring to FIG. 2 in combination, each of the first clamping parts 10 includes a first clamping arm 110 and a supporting arm 120. The first clamping arm 110 is made of an elastic metal material, for example, the first clamping arm 110 is made of a nickel-titanium alloy material to provide a clamping force through the elasticity of the material itself. The supporting arm 120 is made of metal or polymer materials.

The first clamping arm 110 is rotatably connected to the supporting arm 120, e.g., an end of the first clamping arm 110 is pivotally connected to an end of the supporting arm 120 such that the supporting arm 120 can spread the first clamping arm 110 so that the first clamping arm 110 and the supporting arm 120 are movable between an open position (as shown in FIG. 2) and a closed position (as shown in FIG. 1). In a natural state, the first clamping arm 110 and the supporting arm 120 are in a closed position. The supporting arm 120 should have a certain rigidity and flexibility to be able to spread the first clamping arm 110 when in the open position to maintain the open state.

The rotatable connection of an end of the first clamping arm 110 with an end of the supporting arm 120 can be achieved in various ways. For example, the first clamping arm 110 and the supporting arm 120 are connected by a rotating shaft, a pin, a movable hinge, or the like.

Figure 3:
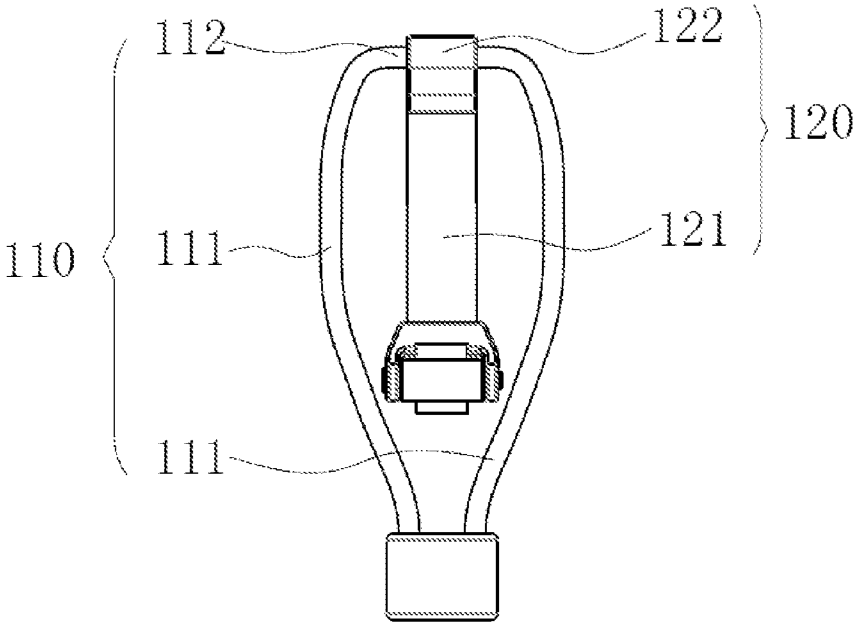
FIG. 3 is a schematic view illustrating a connection relationship between a first clamping arm and a supporting arm according to an embodiment.

In one embodiment, the first clamping arm 110 is generally a wire loop structure having an opening, as shown in FIG. 3. For example, the first clamping arm 110 may be a wire loop having an opening that is formed by a nickel-titanium wire. The supporting arm 120 includes a supporting body 121 and a connecting portion 122 connected to the supporting body 121, and an end of the connecting portion 122 away from the supporting body 121 is connected to the first clamping arm 110. In one embodiment, the connecting portion 122 is integrally formed with the supporting body 121, and an end of the supporting body 121 is wound to form the connecting portion 122. The connecting portion 122 has a containing cavity therein through which the first clamping arm 110 passes, and the two ends of the first clamping arm 110 are curved to form the wire loop having an opening. The first clamping arm 110 and the connecting portion 122 can be pivoted relative to each other. Through the structures of the supporting arm 120 and the first clamping arm 110 themselves cooperating with each other, the first clamping arm 110 and the connecting portion 122 can be pivoted relative to each other without using a coupling member such as a rotating shaft, a pin. This pivotal connection reduces the use of rotating shafts, pins, or the like, and provides for flexible rotation.

In one embodiment, the supporting body 121 is integrally formed with the connecting portion 122, as shown in FIG. 3. The supporting arm 120 including the supporting body 121 and the connecting portion 122 is integrally formed by weaving an elastic wire.

Figure 4:
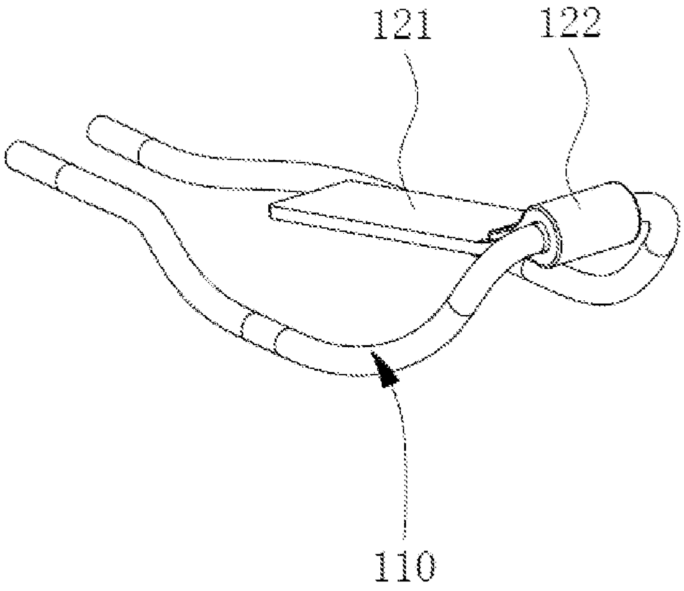
FIG. 4 is a schematic view illustrating a connection relationship between a first clamping arm and a supporting arm according to an embodiment.

In another embodiment, the supporting body 121 is not integrally formed with the connecting portion 122, as shown in FIG. 4. The connecting portion 122 is a machined metal part, and the connecting portion 122 and the supporting body 121 are connected by welding, gluing, crimping, wire sewing, etc. In this way, the supporting arm 120 is not biased during the opening process due to the restriction on two sides of the first clamping arm 110, so as to ensure the smoothness of the opening and closing movements of the first clamping arm 110.

Returning to FIG. 3, in one embodiment, the first clamping arm 110 includes two supporting sections 111 and a connecting section 112, both of which are metal rods. Two ends of the connecting section 112 are connected separately to the two supporting sections 111, and the ends of the two supporting sections 111 away from the connecting section 112 are not connected to form a wire loop structure having an opening. The end where the connecting section 112 is located is a free end of the first clamping arm 110. The supporting arm 120 is rotatably connected to the connecting section 112.

Figure 5:
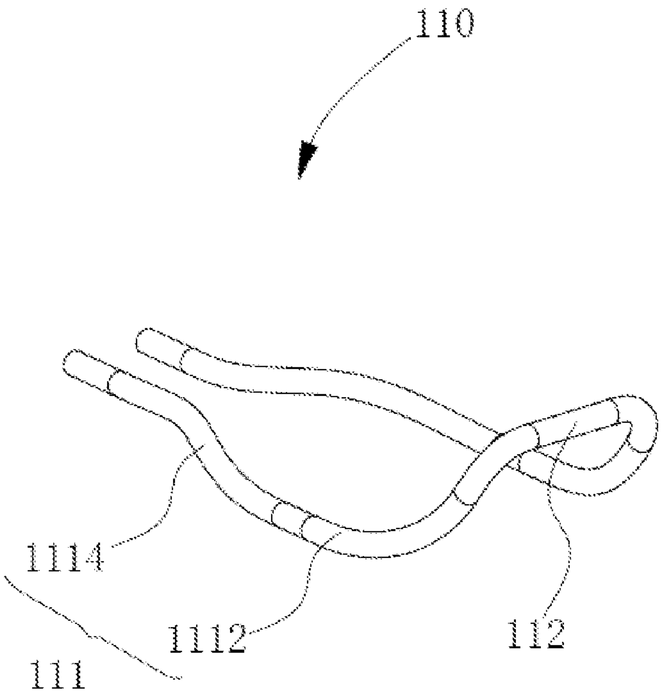
FIG. 5 is a structural diagram of a first clamping arm according to an embodiment.
Figure 6:
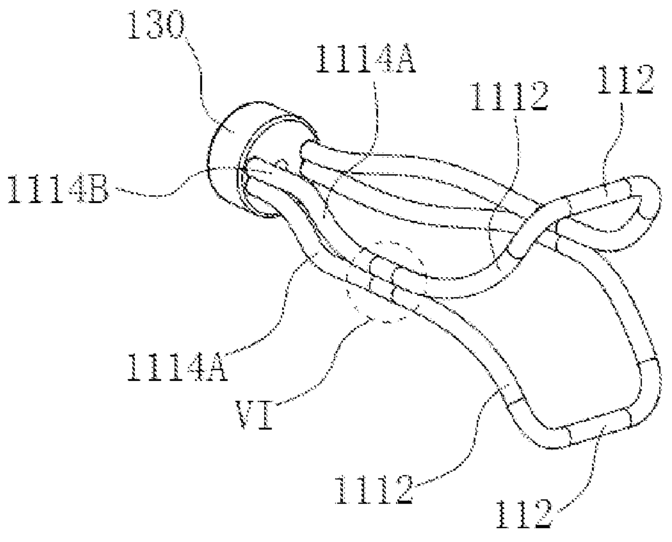
FIG. 6 is a schematic view illustrating a positional relationship of two first clamping arms in a closed state according to an embodiment.

Referring to FIGS. 5 and 6 in combination, in one embodiment, each of the supporting sections 111 includes a curved segment 1112 and an extending segment 1114 connected to the curved segment 1112. An end of the curved segment 1112 away from the extending segment 1114 is curved in a first direction such that the end of the curved segment 1112 away from the extending segment 1114 is not in the same plane as the extending segment 1114. Also, since the end of the curved segment 1112 away from the extending segment 1114 is curved in the first direction, the connecting section 112 of the first clamping arm 110 is away from the longitudinal central axis I-I of the tissue closure device.

As shown in FIG. 6, in a natural state, the curved segment 1112 is curved in the first direction, and the curvature of the curved segment 1112 results in that the end of the curved segment 1112 away from the extending segment 1114 is not in the same plane as the extending segment 1114, so that the free end of each of the two first clamping arms 110 is away from the longitudinal central axis I-I, i.e., the two connecting sections 112 of the two first clamping arms 110 are away from the longitudinal central axis I-I and away from each other, so that the first clamping arms 110 are easily opened. The first direction, e.g., as shown in FIG. 6, may be curved in a direction away from the connecting section 112 of the other first clamping arm 110, and the end of the curved segment 1112 away from the extending segment 1114 is not in the same plane as the extending segment 1114.

In one embodiment, the extending segment 1114 is in a shape of a straight rod, and the connection region of the extending segment 1114 with the curved segment 1112 is in the same plane as the extending segment 1114.

Figure 7:
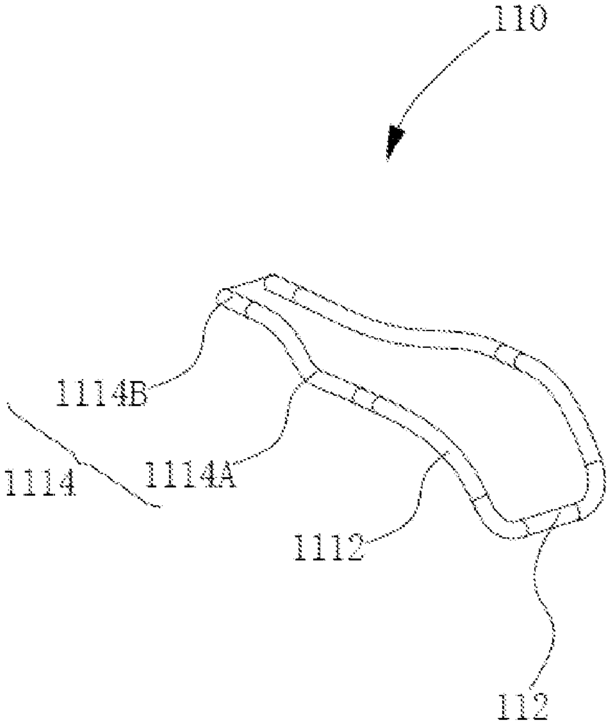
FIG. 7 is a structural diagram of a first clamping arm according to an embodiment.
Figure 8:
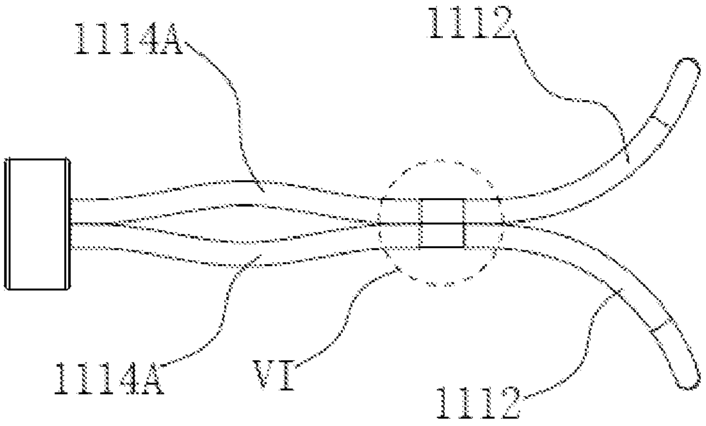
FIG. 8 is a schematic view illustrating a positional relationship of the two first clamping arms shown in FIG. 7 at another perspective.

Referring to FIG. 7, in one embodiment, the extending segment 1114 includes a curved rod 1114A and a straight rod 1114B connected to the curved rod 1114A, and an end of the curved rod 1114A away from the straight rod 11114B is connected to the curved segment 1112. Referring to FIGS. 6 and 8 in combination, in one embodiment, in a natural state (also referred to as a clamped state), the curved rod 1114A is curved in a second direction such that a connection region of the curved rod 1114A with the curved segment 1112 of one first clamping arm 110 abuts reliably against a connection region of the curved rod 1114A with the curved segment 1112 of the other first clamping arm 110 (indicated by the circle at VI in the drawings) to form an abutting region. At the abutting region, since the first clamping arms 110 have elasticity, the two first clamping arms 110 provide opposing abutting forces to each other such that the two first clamping arms 110 abut reliably against each other, which is beneficial to improving the reliability of clamping, so as to prevent the tissue closure device 1 from falling off due to the contraction and relaxation of the heart. The second direction, e.g., as shown in FIG. 7, may be a direction outside the wire loop, i.e., with the circle center of the curved rod 1114A itself being located inside the wire loop.

In one embodiment, the connection region of the curved rod 1114A with the curved segment 1112 of each of the first clamping arms 110 is in a shape of a straight rod, such that the two first clamping arms 110 have an abutting region of a large area and abut against each other reliably.

Figure 9:
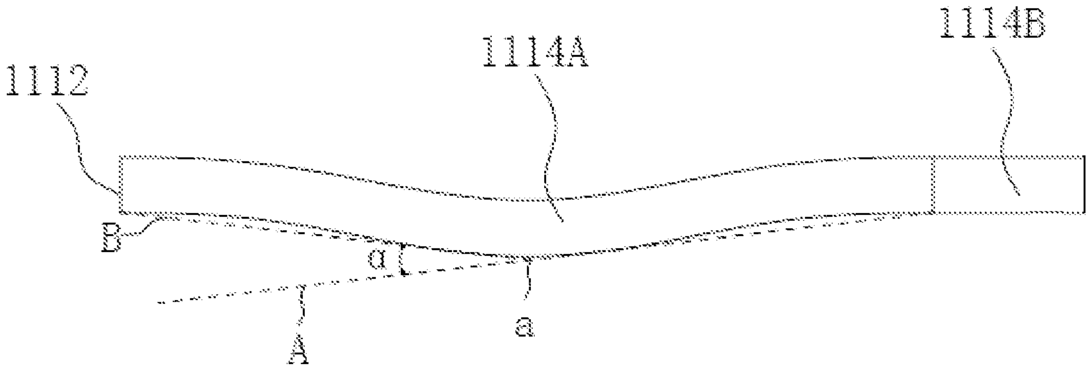
FIG. 9 is a partial structural diagram of a first clamping arm according to an embodiment.

Referring to FIG. 9, in one embodiment, the curved rod 1114A has an angle $\alpha$ between 5 and 15 degrees, so as to allow the connection regions of the extending segments 1114 with the curved segment 1112 of the two first clamping arms 110 to abut reliably against each other. The angle $\alpha$ refers to the angle formed by the intersection of a tangent line A and a tangent line B of the curved rod 1114A, with an intersection point being a. The tangent line A intersects the junction of the curved rod 1114A with the straight rod 1114B, and the tangent line B intersects the junction of the curved rod 1114A with the curved segment 1112.

Figure 10:
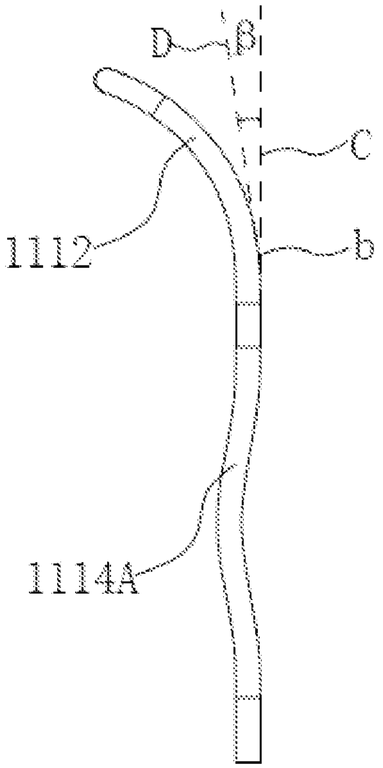
FIG. 10 is a partial structural diagram of a first clamping arm according to an embodiment.

Referring to FIG. 10, in one embodiment, the curved segment 1112 has an angle $\beta$ between 10 and 60 degrees to facilitate opening of the first clamping arm 110. When the length of the curved segment 1112 is constant, the region of the curved segment 1112 that connects with the curved rod 1114A (i.e., the region of the curved segment 1112 that is coplanar with the curved rod 1114A) is long enough to maintain clamping. The angle $\beta$ refers to an included angle between an extension line C of the connection region of the curved rod 1114A with the curved segment 1112 and a tangent line D of the curved segment 1112, and the tangent line D intersects the extension line C at an intersection point b of the extension line C with the curved segment 1112. The intersection point b is a tangent point of the tangent line D.

In one embodiment, the supporting arm 120 is made of an elastic metal material, such as a nickel-titanium alloy material which is made into a clip piece first and one end thereof is then curved and shaped to form the connecting portion 122.

Figure 11:
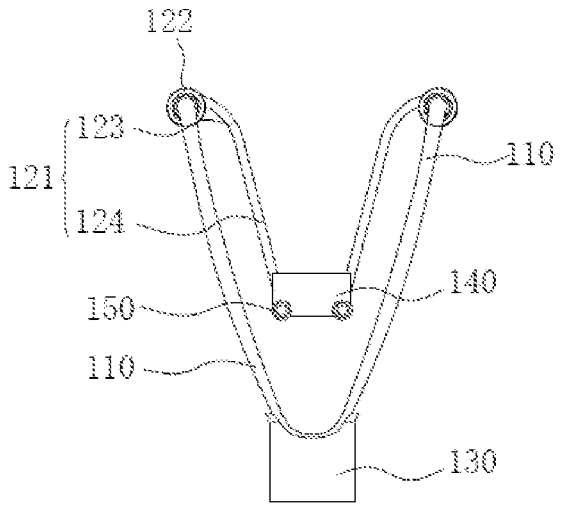
FIG. 11 is a schematic view illustrating a connection relationship of first clamping arms, supporting arms, a first fixing base, and a second fixing base according to another embodiment.
Figure 12:
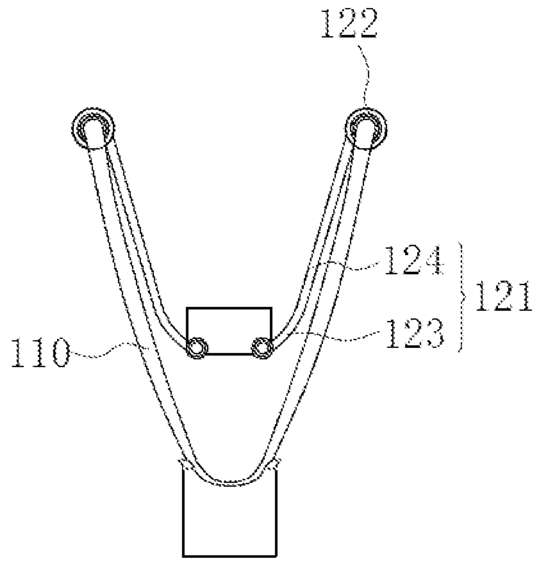
FIG. 12 is a schematic view illustrating a connection relationship of first clamping arms, supporting arms, a first fixing base, and a second fixing base of a tissue closure device according to another embodiment.

Referring to FIG. 11, in one embodiment, the supporting body 121 includes a curved section 123 and a straight section 124. One end of the curved section 123 is fixedly connected to the straight section 124, and the other end is rotatably connected to the first clamping arm 110. In one embodiment, the connecting portion 122 is connected to an end of the curved section 123 away from the straight section 124, and the curved section 123 is rotatably connected to the first clamping arm 110 via the connecting portion 122. In another embodiment, as shown in FIG. 12, an end of the connecting portion 122 is connected to an end of the straight section 124 away from the curved section 123, and the straight section 124 is rotatably connected to the first clamping arm 110 via the connecting portion 122.

Figure 13:
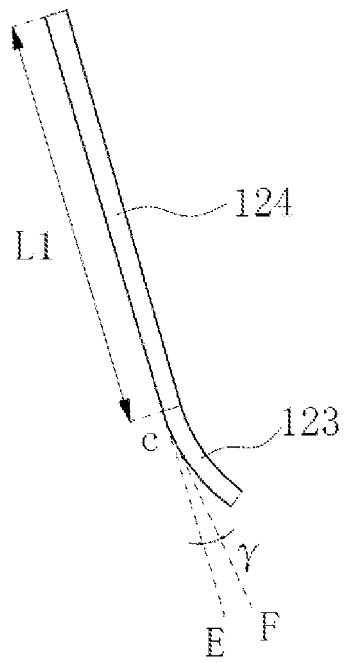
FIG. 13 is a structural diagram of a supporting arm of a tissue closure device according to an embodiment.

Referring to FIG. 13, in one embodiment, the straight section 124 has a length L1 and the curved section 123 has an arc length L2 (not shown), where $L2/L1=1/5-1/3$. The lengths of the straight section 124 and the curved section 123 are set in this way such that, on the one hand, the curved section 123 is prevented from being excessively long so as to ensure that a sufficient spreading force is transmitted to the first clamping arm 110, i.e., ensuring that the supporting arm 120 can provide a spreading force such that the first clamping arm 110 can be spread during the opening process, on the other hand, the curved section 123 is prevented from being excessively short such that the curved section 123 can be further deformed (further curved) during the opening process to alleviate the excessive stress.

With continued reference to FIG. 13, in one embodiment, the curved section 123 has an angle $\gamma$ ranging from 10 to 45 degrees which ensures that the supporting arm 120 can transmit the spreading force to the first clamping arm 110 under a certain force, and that the curved section 123 can deform to some extent to alleviate the excessive stress. The angle $\gamma$ refers to an included angle between an extension line E of the straight section 124 and a tangent line F of the curved section 123, and the tangent line F intersects the extension line E at an intersection point c of the extension line E with the curved section 123. The intersection point c is a tangent point of the tangent line F.

When the length of the supporting body 121 is determined, a greater angle $\gamma$ of the curved section 123 may cause a smaller captured length of the supporting body 121, making it more difficult to capture the tissue. An excessively small angle $\gamma$ of the curved section 123 may make it difficult to easily open the first clamping arm 110 to function. Therefore, in one embodiment, the straight section 124 has a length L1 and the curved section 123 has an arc length L2, where $L2/L1=1/5-1/3$. The curved section 123 has an angle $\gamma$ ranging from 10 to 45 degrees so as to easily open the first clamping arm 110 and capture the tissue, facilitating the operation and the surgery, reducing the operation time.

In one embodiment, the supporting body 121 may be a one-piece structure made of wire or sheet materials which, after the heat-setting, produce corresponding curved shapes to form the curved section 123 and the straight section 124.

Returning to FIG. 11, in one embodiment, the tissue closure device 1 further includes a first fixing base 130 and a second fixing base 140. The first fixing base 130 and the second fixing base 140 are axially opposed and coaxial and spaced apart.

An end of the first clamping arm 110 away from the supporting arm 120 is fixedly connected to the first fixing base 130. The fixed connection may be completed in ways known to those skilled in the art, including, but not limited to, welding, gluing, crimping, wire sewing. In the embodiment, the first clamping arm 110 is connected to the first fixing base 130 via the supporting section 111. An end of the straight rod 1114B of the supporting section 111 away from the curved rod 1114A is fixedly connected to the first fixing base 130, as shown in FIG. 7. Referring again to FIG. 11, an end of the supporting arm 120 away from the first clamping arm 110 is rotatably connected to the second fixing base 140. The supporting body 121 and the second fixing base 140 are connected by a rotating shaft, a pin, a movable hinge, or the like. For example, the supporting body 121 is rotatably connected to the second fixing base 140 via the rotating shaft 150.

In one embodiment, as shown in FIG. 11, an end of the straight section 124 of the supporting body 121 away from the curved section 123 is rotatably connected to the second fixing base 140.

In one embodiment, as shown in FIG. 12, an end of the curved section 123 of the supporting body 121 away from the straight section 124 is rotatably connected to the second fixing base 140.

In one embodiment, the central portions of both the first fixing base 130 and the second fixing base 140 are formed with through holes.

Returning to FIG. 2, in one embodiment, each of the second clamping parts 20 includes a second clamping arm 210, where one end of the second clamping arm 210 is connected to the second fixed fixing base 140, and the other end is a free end. When the first clamping arm 110 and the supporting arm 120 are in the closed position, the free end of the second clamping arm 210 is close to the supporting arm 120, thereby clamping the tissue between the second clamping arm 210 and the supporting arm 120.

In another embodiment, an end of the second clamping arm 210 is not connected to the second fixing base 140, but is instead connected to an end of the supporting arm 120 away from the first clamping arm 110.

The second clamping arm 210 is made of an elastic material such that the second clamping arm 210 has elasticity. The tissue is located between the first elastic clamping arm 110 and the second elastic clamping arm 210 and is elastically squeezed, such that the tissue closure device 1 has a stable clamping performance. In one embodiment, the second clamping arm 210 is made of a nickel-titanium alloy material.

In one embodiment, each of the second clamping parts 20 further includes an anchor 220. The anchor 220 is arranged on a surface of the second clamping arm 210 facing the supporting arm 120 and extends toward the supporting arm 120. The anchor 220 is used to capture tissue (e.g., leaflets) on the one hand, and on the other hand, when the tissue is captured, the anchor 220 penetrates into the tissue, and the first and second clamping arms 110, 210 and the anchor 220 cooperate to reliably clamp the tissue.

There may be one or more anchor(s) 220. When there is a plurality of anchors 220, they are spaced apart on the second clamping arms 210.

There are two first clamping parts 10 and two second clamping parts 20, and the two first clamping parts 10 are symmetrically arranged on two sides of the first fixing base 130 with the longitudinal central axis of the first fixing base 130 (coinciding with the longitudinal central axis I-I) being a center of symmetry. In the embodiment, the two first clamping arms 110 are symmetrically arranged on the two sides of the first fixing base 130, and the two supporting arms 120 are symmetrically located on two sides of the second fixing base 140. One end of each of the supporting arms 120 is rotatably connected to the first clamping arm 110, and the other end is rotatably connected to the second fixing base 140. The two second clamping arms 210 are symmetrically arranged on the two sides of the second fixing base 140 with the longitudinal central axis of the second fixing base 140 (coinciding with the longitudinal central axis I-I) being a center of symmetry.

With continued reference to FIG. 2, the tissue closure device 1 further includes a spacer 160. The spacer 160 has one end connected to the second fixing base 140 and the other end extending axially away from the second fixing base 140 and the first fixing base 130.

The spacer 160 is a cage-like structure made of an elastic material such as an elastic wire or an elastic polymer wire. In one embodiment, the spacer 160 is a cage-like structure woven from a nickel-titanium alloy wire. In another embodiment, the spacer 160 is made of elastic sponge or elastic silicone. In one embodiment, the spacer 160 is a bladder structure made of a polymer material.

The spacer 160 can seal and fill the gap between the two tissues, further improving the sealing performance. Further, since the spacer 160 is made of an elastic material, the spacer 160 has a certain flexibility and deformability. After clamping, the spacer 160 can play a buffering role, so that the two tissues that are clamped (such as two valve leaflets) are not drawn together toughly, thereby reducing the clamping stress.

The shape of the spacer 160 is not limited, and any shape capable of performing a sealing and buffering function may be used. In one embodiment, the spacer 160 is cylindrical. In another embodiment, the spacer 160 is small at axially opposite ends and large in the middle.

In one embodiment, the shape of the spacer 160 matches the shape of the first clamping arm 110 such that in the clamped state, the outer surface of the spacer 160 completely fills the wire loop of the first clamping arm 110, thereby improving the sealing effect.

In one embodiment, the spacer 160 is provided with a cover film (not shown) that covers the surface of the spacer 160 to further improve the sealing effect.

The transporter is used to transport the tissue closure device 1 to a target site and to release the tissue closure device 1 to clamp a target tissue.

Figure 14:
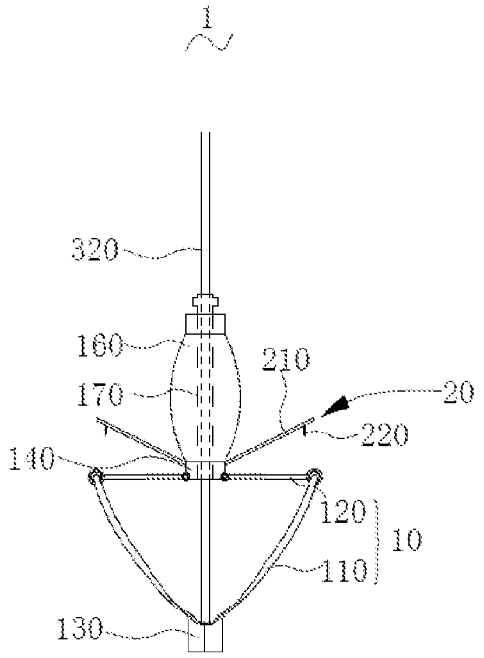
FIG. 14 is a structural diagram of a tissue closure device in an open state according to an embodiment.
Figure 15:
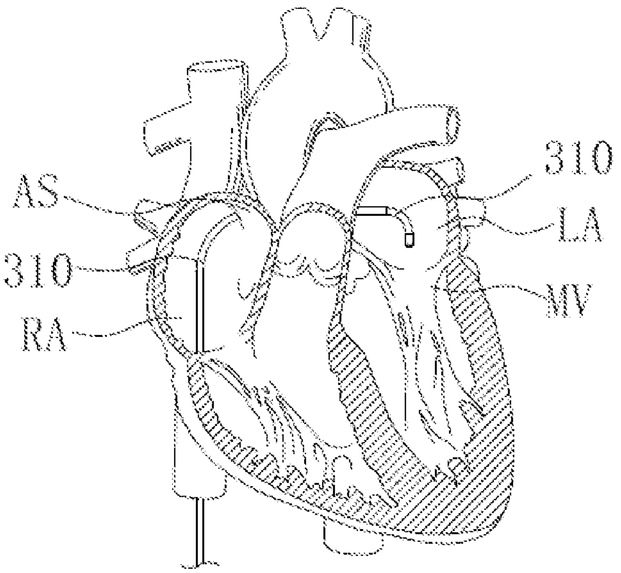
FIG. 15 is a schematic view illustrating an implantation process of a tissue closure device according to an embodiment.

Referring to FIGS. 14 and 15 in combination, the transporter includes a handle (not shown), a transporting sheath 310, and a lever 320. The handle is connected to a proximal end of the transporting sheath 310, and a control for operating the tissue closure device 1 is provided on the handle. The radially compressed tissue closure device 1 is contained within the transporting sheath 310 and reaches the target site along with the transporting sheath 310. The lever 320 is contained in the transporting sheath 310. The lever 320 has a proximal end connected to the control and a distal end passing through the spacer 160 and the second fixing base 140 and extending to the first fixing base 130. The distal end of the lever 320 is detachably connected to the first fixing base 130. The detachable connection includes, but is not limited to, a threaded connection, for example, the through-hole of the first fixing base 130 is a threaded hole, and the outer wall of the distal end of the lever 320 is provided with an external thread to achieve the detachable connection.

The transporter further includes a coupling member that is detachably connected to the distal end of the spacer 160. The coupling member may take any structure known to those skilled in the art that is capable of being detachably connected to the spacer 160. For example, in one embodiment, the coupling member is a cannula with an internal thread at the distal end, and the cannula is contained within the transporting sheath 310. The spacer 160 is provided with a thread structure adapted to the cannula, so as to achieve detachable connection.

Figure 16:
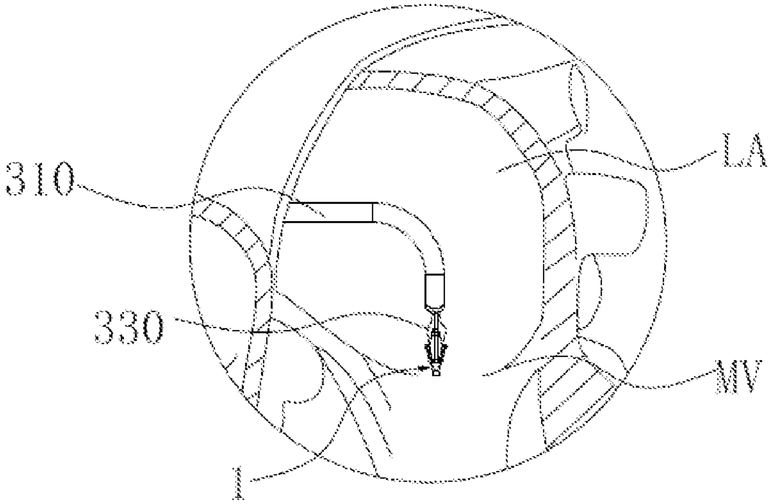
FIG. 16 is a schematic view illustrating an implantation process of a tissue closure device according to an embodiment.

As shown in FIG. 16, the transporter further includes control wires 330 which pass through the transporting sheath 310. The control wires 330 have proximal ends connected to the control and distal ends detachably connected to the second clamping arms 210. The control wires 330 control the movement of the second clamping arms 210 to capture the target tissue.

In one embodiment, in order to facilitate the lever 320 to sequentially pass through the second fixing base 140 and the first fixing base 130 via the spacer 160, a guide tube 170 having a lumen is provided inside the spacer 160, as shown in FIG. 14. The guide tube 170 extends axially from the distal end to the proximal end of the spacer 160. The lever 320 passes through the lumen of the guide tube 170, through the second fixing base 140, and extends to the first fixing base 130.

Meanwhile, the guide tube 170 may support the spacer 160 to maintain the structural stability of the spacer 160.

Figure 17:
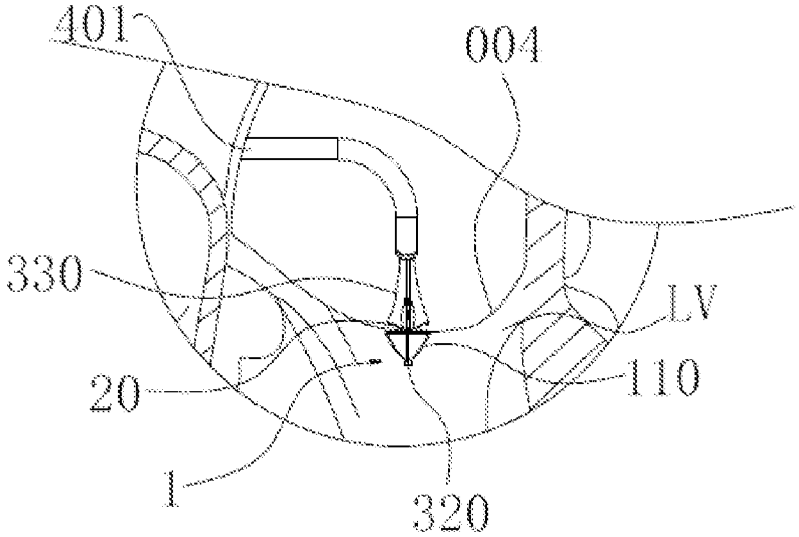
FIG. 17 is a schematic view illustrating an implantation process of a tissue closure device according to an embodiment.
Figure 18:
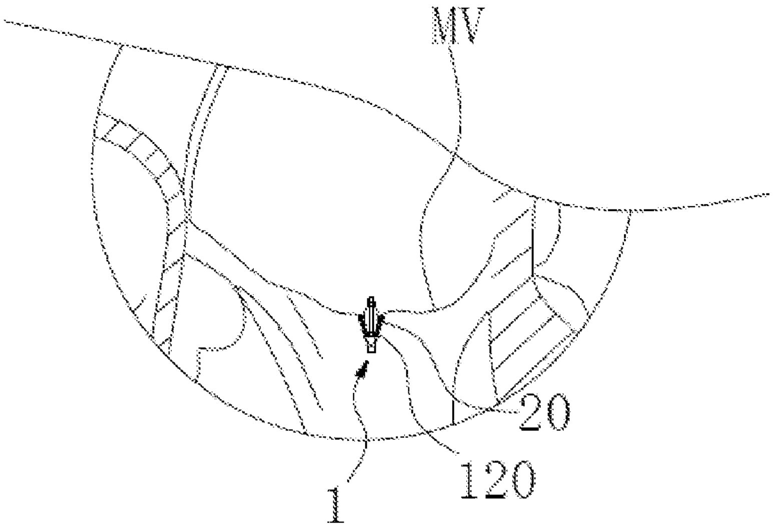
FIG. 18 is a schematic view illustrating an implantation process of a tissue closure device according to an embodiment.

The transportation, release, and closure processes of the tissue closure device 1 is described with the tissue to be closed being mitral valve leaflets as an example. In one embodiment, as shown in FIG. 15, the transporting sheath 310 passes through the femoral vein and the inferior vena cava to the right atrium RA, and then punctures the atrial septum AS, so that the distal end of the transporting sheath 310 reaches the left atrium LA. The tissue closure device 1 is advanced out of the transporting sheath 310 by adjusting the distal end of the transporting sheath 310 to be centered over the mitral valve MV and then manipulating the control on the handle, as shown in FIG. 16. Further, referring to FIG. 17, the tissue closure device 1 is advanced to the mitral valve MV position and its position is adjusted (if necessary) so that the first clamping arms 110 of the tissue closure device 1 are located on a side of the mitral valve leaflets close to the left ventricle LV. By manipulating the control on the handle, the lever 320 is moved axially so that the first clamping arms 110 are in an open state to capture the leaflets. The angle of the second clamping parts 20 is then controlled by the control wire 330 to capture the leaflets. After the second clamping parts 20 capture the valve leaflets, the lever 320 is moved axially such that the supporting arms 120 and the second clamping parts 20 move toward each other and abut against the spacer 160 to clamp the valve leaflets. The two second clamping parts 20 and the two supporting arms 120 cooperate to clamp the anterior and posterior leaflets of the mitral valve MV as shown in FIG. 18, thereby reducing the opening area of the mitral valve MV. After the clamping is completed, the control wire 330 is withdrawn, the lever 320 is disconnected from the first fixing base 130, the coupling member is disconnected from the spacer 160, and the transporter is withdrawn, thereby completing the operation.

Figure 19A:
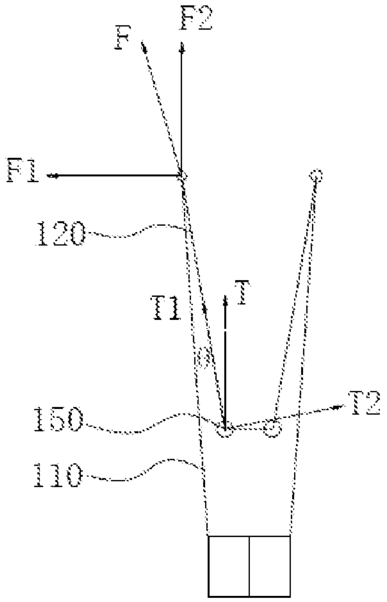
FIG. 19*a* is a schematic view illustrating a force analysis of a first clamping arm and a supporting arm of a conventional structure.

During the opening process of a first clamping arm 110, the force analysis for a supporting arm 120 is as follows when the supporting arm 120 is in a conventional structure:

As shown in FIG. 19*a*, the first clamping arm 110 is opened by sliding the lever 320 and the guide tube 170 relative to each other. T is a force applied by the guide tube 170 to the rotating shaft 150, and T generates two component forces: a component T1 parallel to the supporting arm 120 and a component T2 perpendicular to the supporting arm 120. T1 is transmitted along the supporting arm 120 to a position where the supporting arm 120 is rotatably connected to the first clamping arm 110 to drive the first clamping arm 110 to open. Assuming that there is no loss of the force when it is transmitted within the supporting arm 120, T1=F. F is decomposed into two component forces at the position where the supporting arm 120 is rotatably connected to the first clamping arm 110, i.e., a component F1 perpendicular to the first clamping arm 110 and a component F2 parallel to the direction of the first clamping arm 110. F1=F*Sin θ and T1=T*Cos θ, where θ is an included angle between the supporting arm 120 and the first clamping arm 110. From the above, it can be calculated that T=T1/Cos θ=F/Cos θ=(F1/Sin θ)/Cos θ=F1/(Sin θ*Cos θ)=2*F1/Sin 2θ.

Figure 19B:
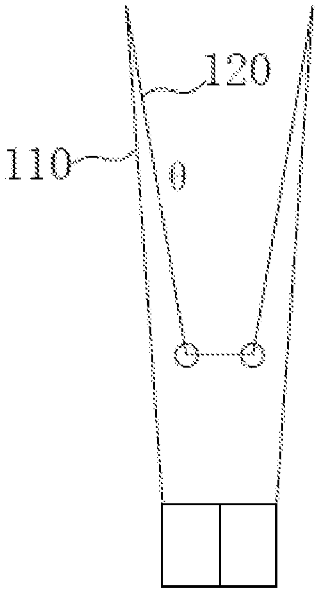
FIG. 19*b* is a schematic view illustrating different degrees of open states of a first clamping arm and a supporting arm of a conventional structure.
Figure 19C:
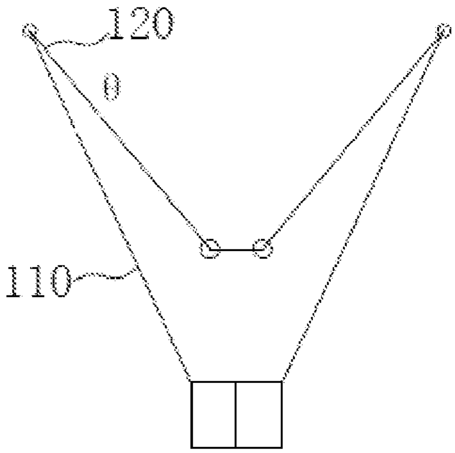
FIG. 19*c* is a schematic view illustrating different degrees of open states of a first clamping arm and a supporting arm of a conventional structure.
Figure 19D:
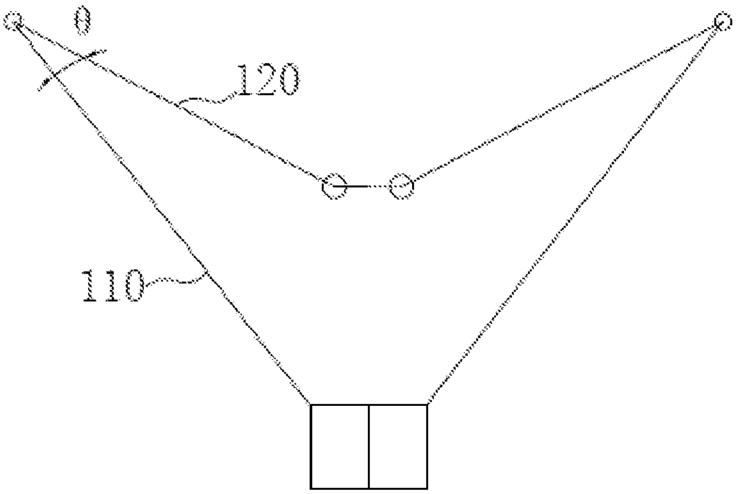
FIG. 19*d* is a schematic view illustrating different degrees of open states of a first clamping arm and a supporting arm of a conventional structure.

As can be seen from the above formula, as the angle θ increases, less force needs to be applied to the guide tube 170. As shown in FIG. 19*b*, θ is 20 degrees. As shown in FIG. 19*c*, θ is 40 degrees. As shown in FIG. 19*d*, θ is 65 degrees. From FIG. 19*b* to FIG. 19*d*, less and less force needs to be applied to the guide tube 170. The angle θ is smallest when the first clamping arm 110 and the supporting arm 120 are in a closed position. In the case where the spreading force F1 is constant, the force needs to be applied to the lever 320 is greatest. In the closed position, the angle θ is 1-10 degrees. When 0 is 10 degrees and the force F1 for spreading the supporting arm 120 is 10 N, T1 is calculated as 58 N. The guide tube 170 needs to bear the force of the supporting arms 120 on both sides, so the actual force required on the guide tube 170 is 2*T1=116 N. It can be seen that during opening process of the first clamping arms 110, the guide tube 170 and the lever 320 have to bear a large force. Therefore, the first clamping arms 110 need to be opened under a large force, and thus, on the one hand, a doctor needs to apply a large force, which increases the surgical risk; on the other hand, the risk of failure of the stressed components of the tissue closure device 1 is increased.

The supporting bodies 121 of the tissue closure device 1 include curved sections 123 and straight sections 124. That is, in a natural state (a closed state in which the first clamping arms 110 and the supporting arms 120 are in a closed position), an end of each of the supporting arms 120 is curved. Whether the curved sections 123 are rotatably connected to the first clamping arms 110 or the curved sections 123 are connected to the second fixing base 140, the component forces of the supporting arms 120 which are decomposed in a direction perpendicular to the first clamping arms 110 increase because of the curved sections 123 when the supporting arms 120 spread the first clamping arms 110, and therefore the force applied to the lever 320 and the guide tube 170 decreases, thus achieving the purpose of saving effort, facilitating the operation and an easy control, and improving the safety of the operation.

In one embodiment, the degree of curvature of the curved sections 123 increases as the first clamping arms 110 and the supporting arms 120 move from the closed position to the open position. That is, the curved sections 123 can guide the supporting arms 120 to deform in the curved direction when the force exceeds a certain limit, so as to play a buffering role. When the supporting arms 120 are deformed to a certain extent, the first clamping arms 110 open more easily.

During implantation, the first clamping arms 110 and the supporting arms 120 of the tissue closure device 1 change from a closed position to an open position. After capturing the tissue, the first clamping arms 110 and the supporting arms 120 change from the open position to the closed position such that the first clamping arm 110 and the second clamping parts 20 get close to each other so that the tissue is clamped between the first clamping arms 110 and the second clamping parts 20. Since the supporting arms 120 of the tissue closure device 1 include curved sections 123 and straight sections 124, the component forces applied by the supporting arms 120 in the opening directions of the first clamping arms 110 are increased during the opening process, so that the first clamping arms 110 are opened more easily, thereby improving the safety of the manipulation system.

Further, due to the special structural design of the first clamping arms 110, the free ends of the two first clamping arms 110 are away from the longitudinal central axis I-I, so that the first clamping arms 110 open easily, and the supporting arms 120 may spread the first clamping arms 110 with a small force, so that the connecting sections 112 of the first clamping arms 110 move in a direction away from the longitudinal central axis I-I so as to open the first clamping arms 110.

Also, since the ends of the curved segments 1112 of the first clamping arms 110 close to the extending segments 1114 are in the same plane as the extending segments 1114, the two first clamping arms 110 of the two second clamps 10 can reliably clamp the spacer 160 in the closed position to avoid falling off and maintain the sealing performance.

Various features of the embodiments above can be combined in any of a variety of manners. In order to make the description concise, not all the possible combinations of the features in the embodiments above are described. However, the combinations of these features shall be considered as falling with the scope of the embodiments as long as there is no contradiction therein.

The embodiments described above express only a few implementations which are described in detail and should not therefore be construed as limiting. It is noted that a person of ordinary skill in the art would be able to make several variations and improvements without departing from the concept and scope of the embodiments.

The invention claimed is:

1. A tissue closure device, comprising:

first clamping parts and second clamping parts configured to clamp tissue, wherein each of the first clamping parts comprises a first clamping arm comprising a connecting section and two supporting sections; two ends of the connecting section are separately connected to the two supporting sections, and the end where the connecting section is located is a free end of the first clamping arm;

each of the supporting sections comprises a curved segment and an extending segment;

one end of the curved segment is connected to the extending segment, and the other end is connected to the connecting section; and an end of the curved segment away from the extending segment is not in the same plane as the extending segment, so that the connecting section is away from the longitudinal central axis of the tissue closure device;

wherein each of the first clamping parts further comprises a supporting arm having an end rotatably connected to the connecting section;

wherein the tissue closure device further comprises a first fixing base and a second fixing base, wherein an end of the first clamping arm away from the supporting arm is fixedly connected to the first fixing base, and an end of the supporting arm away from the first clamping arm is rotatably connected directly to the second fixing base; and wherein the first fixing base and the second fixing base are axially opposed, coaxial, and spaced apart.

2. The tissue closure device according to claim 1, wherein the extending segment comprises a curved rod and a straight rod connected to the curved rod, and wherein an end of the curved rod away from the straight rod is connected to the curved segment.

3. The tissue closure device according to claim 2, wherein there are two first clamping parts and two second clamping parts, and a connection region of the curved rod with the curved segment of one first clamping arm abuts against a connection region of the curved rod with the curved segment of the other first clamping arm.

4. The tissue closure device according to claim 2, wherein the curved rod has an angle between 5 and 15 degrees or the curved segment has an angle between 10 and 60 degrees.

5. The tissue closure device according to claim 2, wherein the connection region of the curved rod with the curved segment of the first clamping arms is in a shape of a straight rod, such that the two first clamping arms have an abutting region of a large area.

6. The tissue closure device according to claim 1, wherein the supporting arm comprises a supporting body comprising a curved section and a straight section;

one end of the curved section is fixedly connected to the straight section, and the other end is rotatably connected to the first clamping arm; or an end of the curved section is fixedly connected to the straight section, and an end of the straight section away from the curved section is rotatably connected to the first clamping arm; and the first clamping arm and the supporting arm are movable between an open position and a closed position, and when the first clamping arm and the supporting arm are in the closed position, the first clamping arm and the second clamping part are close to each other, wherein the curved section is curved in the closed position, and when the first clamping arm and the support arm move from the closed position to the open position, the curved section can be further deformed and curved, increasing the degree of curvature of the curved section.

7. The tissue closure device according to claim 1, wherein the supporting arm further comprises a connecting portion connected to a supporting body, and wherein an end of the connecting portion away from the supporting body is connected to the first clamping arm, and an end of the supporting body away from the connecting portion is rotatably connected directly to the second fixing base.

8. The tissue closure device according to claim 7, wherein the supporting body is not integrally formed with the connecting portion, and the connecting portion and the supporting body are connected by at least one method among welding, gluing, crimping, and wire sewing.

9. The tissue closure device according to claim 1, further comprising a spacer having one end fixedly connected to the second fixing base and the other end extending axially in a direction away from the second fixing base.

10. The tissue closure device according to claim 1, wherein the first clamping arm is made of an elastic metal material, which provides clamping force through the elasticity of the material itself; and/or, wherein the supporting arm is made of an elastic metal material.

* * * * *